(12) United States Patent
Gahman

(10) Patent No.: US 10,874,444 B2
(45) Date of Patent: Dec. 29, 2020

(54) HINGE PLATE ASSEMBLY

(71) Applicant: GLOBUS MEDICAL, INC., Audubon, PA (US)

(72) Inventor: Kevin Gahman, Douglassville, PA (US)

(73) Assignee: Globus Medical, Inc., Audubon, PA (US)

( * ) Notice: Subject to any disclaimer, the term of this patent is extended or adjusted under 35 U.S.C. 154(b) by 183 days.

(21) Appl. No.: 15/794,032

(22) Filed: Oct. 26, 2017

(65) Prior Publication Data
US 2019/0125419 A1 May 2, 2019

(51) Int. Cl.
| | | |
|---|---|---|
| *A61B 17/56* | (2006.01) | |
| *A61B 17/58* | (2006.01) | |
| *A61B 17/80* | (2006.01) | |
| *A61F 2/30* | (2006.01) | |
| *A61B 17/86* | (2006.01) | |

(52) U.S. Cl.
CPC ...... *A61B 17/8085* (2013.01); *A61B 17/8023* (2013.01); *A61B 17/86* (2013.01)

(58) Field of Classification Search
CPC combination set(s) only.
See application file for complete search history.

(56) References Cited

U.S. PATENT DOCUMENTS

2010/0274248 A1\* 10/2010 Overes ............... A61B 17/7059
606/71
2016/0000482 A1\* 1/2016 Ehmke ............... A61B 17/8009
606/71

\* cited by examiner

*Primary Examiner* — Sameh R Boles

(57) ABSTRACT

Securing plate assemblies, systems, and methods thereof. A hinge plate assembly includes a first body portion having a groove extending into the first body and a second body portion having a tongue extending outwardly therefrom and inserted into the groove. A securing member secures the tongue in the groove.

9 Claims, 5 Drawing Sheets

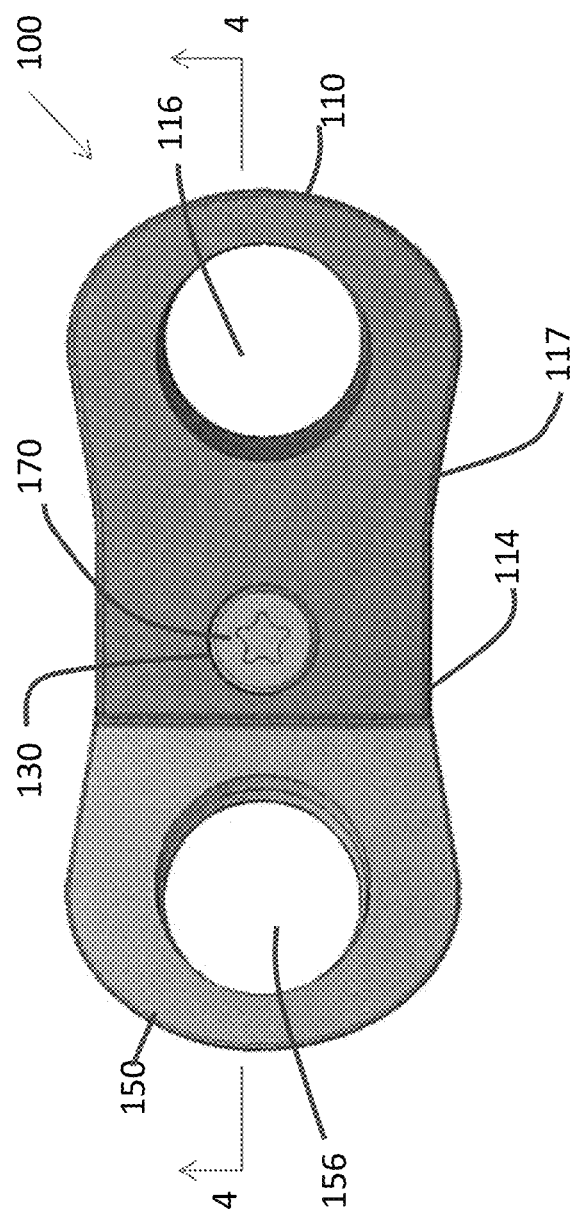
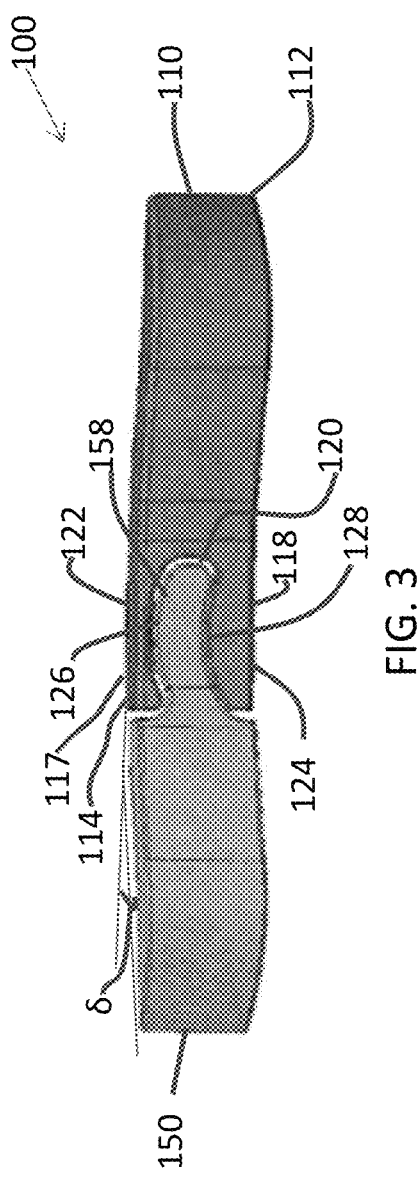

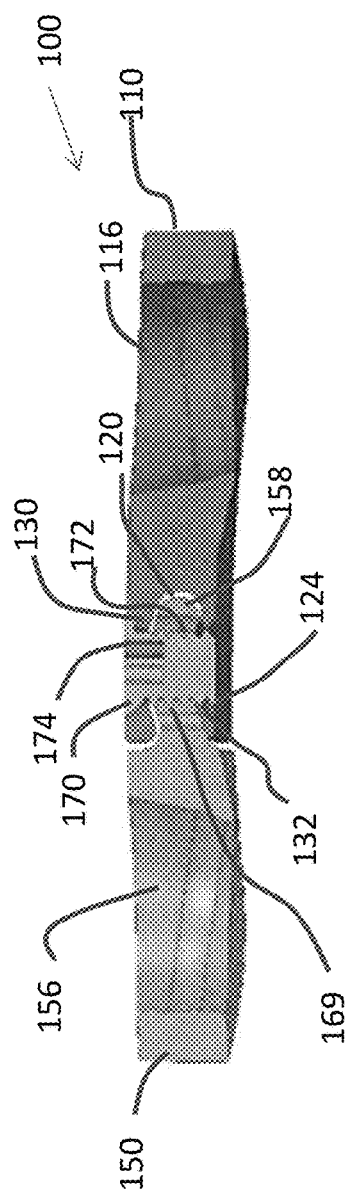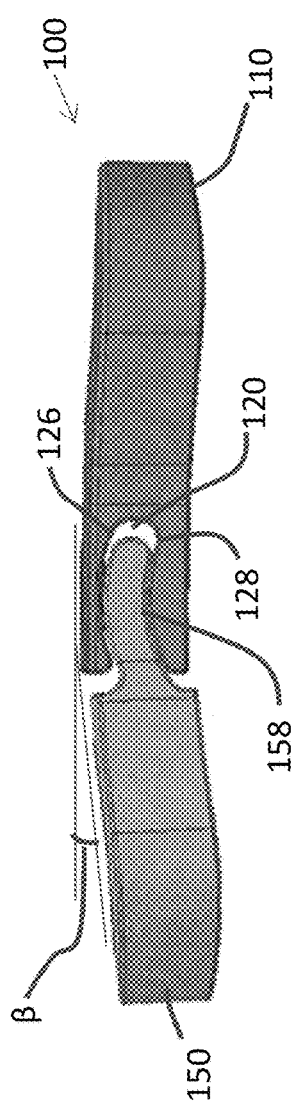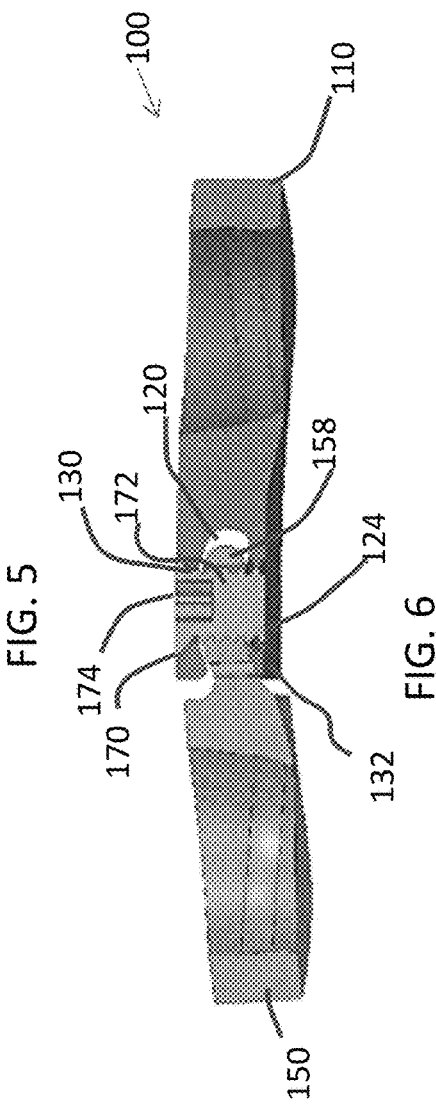

HINGE PLATE ASSEMBLY

BACKGROUND

Field of the Invention

The present invention relates to hinge plates, assemblies, and systems that are used to secure two adjoining bone portions to each other and related methods of use.

Description of the Related Art

Fixation plates are used to secure two adjacent bone portions together, whether the portions are two pieces of a single, but broken, bone, or two different bones. Because of an infinite variability in patient anatomy, these plates often need to be bent and manipulated to more closely approximate the anatomical structures relevant to the procedure being performed.

Accordingly, there exists a need for a fixation plate that can be quickly and easily adjusted to conform to a patient's anatomy.

SUMMARY

To meet this and other needs, hinge plates, assemblies, systems, and methods of use are provided. The hinge plate may include one or more hinge plate portions connected or configured to be moveable or adjustable relative to one another, thereby allowing for better conformity with the anatomical structures which the hinge plate aligns with or contacts.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

According to one embodiment, a hinge plate assembly may include a plurality of hinge plates configured to secure adjacent bone portions to each other.

In one embodiment, the hinge plate assembly comprises a first body portion having a groove extending into the first body and a through-opening extending therethrough and in communication with the groove. A second body portion has a tongue extending outwardly therefrom and inserted into the groove. A securing member extends through the through-opening for engagement with the tongue to secure the tongue in the groove.

In an alternative embodiment, the hinge plate assembly includes a first body portion having a first screw end and a groove end and a second body portion having a second screw end and a tongue end. The tongue end is inserted into the groove end. A securing member extends through the groove end and the tongue end such that the securing member secures the tongue end in the groove end.

In still another alternative embodiment, the hinge plate assembly includes a first body portion having an arcuate groove extending into the first body and a second body portion having an arcuate tongue extending outwardly therefrom and inserted into the groove. A securing member secures the tongue in the groove.

In yet another embodiment, the hinge plate assembly may be installed with one or more fasteners to adjacent portions of bone (e.g., two portions of a broken bone or two separate or different bones). The hinge plate assembly may be adjusted to conform to the patient anatomy before or during implantation.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 2 is a top plan view of the hinge plate assembly of FIG. 1, without mounting fasteners or screws;

FIG. 3 is a side elevational view of the hinge plate assembly of FIG. 2;

FIG. 4 is a sectional view of the hinge plate assembly of FIG. 2, taken along lines 4-4 of FIG. 2;

FIG. 5 is a side elevational view of the hinge plate assembly of FIG. 2, with the hinge bodies making up the hinge assembly spread apart;

FIG. 6 is a sectional view of the hinge plate assembly of FIG. 5;

DETAILED DESCRIPTION

Figure 1:
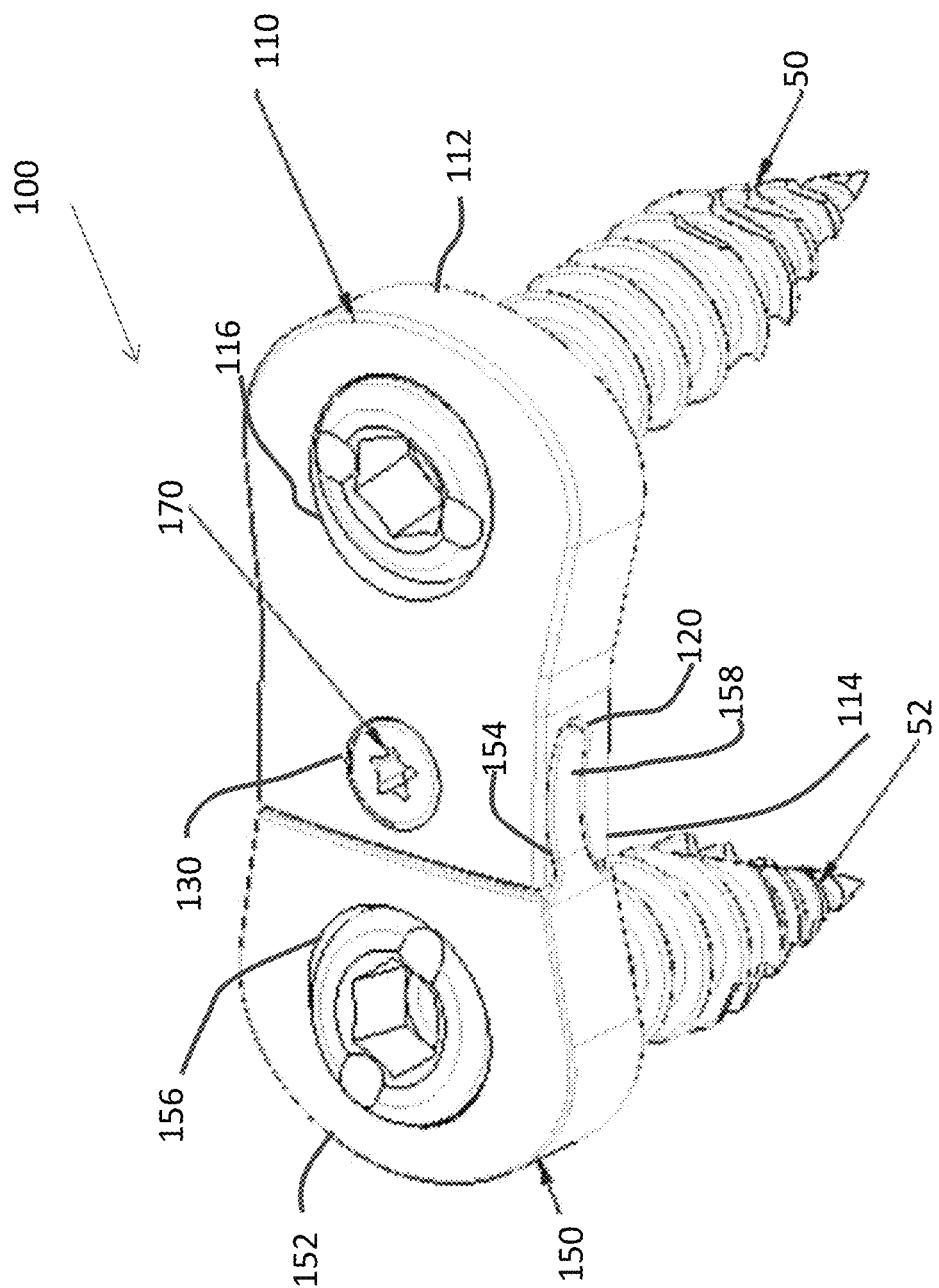
FIG. 1 is a perspective view of a hinge plate assembly according to a first exemplary embodiment.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

Also for purposes of this description, the terms "couple," "coupling," "coupled," "connect," "connecting," or "connected" refer to any manner known in the art or later developed of joining or connecting two or more elements directly or indirectly to one another, and the interposition of one or more additional elements is contemplated, although not required. Conversely, the terms "directly coupled," "directly connected," etc., imply the absence of such additional elements.

The present disclosure provides embodiments of hinge plate devices, assemblies, and systems that can be used to secure two adjacent bone portions to each other and the related methods thereof. The bone portions can be two pieces of a single, but broken, bone that is being repaired, such as, for example, a broken bone, such as a broken tibia. Alternatively, the bone portions can be separate bones that are being fixedly connected, or fused, to each other, such as, for example, adjacent vertebrae. The bone may include long bones, short bones, flat bones, irregular bones, and sesamoids. Suitable long bones may include the humerus, radius, ulna, femur, tibia, or the like. The devices and assemblies stabilize bony structures with bone fasteners, screws, or other means of fixation inserted through, around, or on the plates or portions thereof. The plate bodies can be constructed from known biocompatible materials including, but not limited to, commercially pure titanium, titanium alloys, stainless steel, poly-ether-ether-ketone ("PEEK"), or other biocompatible materials.

According to one aspect, the hinged plate assemblies save a surgeon or other medical professional the step of having to pre-bend plates to match patient anatomy, minimize indecisions on how to pre-bend plates, and/or minimize errors made while bending the plates. Additionally, the plates may provide a closer approximation to patient anatomy than traditional static plates. According to one embodiment, a hinge plate assembly may include first and second articulating hinge bodies, with a securing device to securely fix the hinge bodies to each other once a desired relative position between the first and second plate portions is obtained.

Referring to FIGS. 1-6, a hinge plate assembly 100 ("assembly 100") according to a first exemplary embodiment is shown. Assembly 100 includes a first body portion 110 hingedly connected to a second body portion 150. A securing member 170 secures first body portion 110 and second body portion 150 to each other.

First body portion 110 includes a first fastener or screw end 112 and a groove end 114, distal from the first screw end 112. First screw end 112 includes a first fastener or screw hole 116 extending therethrough such that a fixation fastener or screw 50 can be inserted through first screw hole 116 and into a first bone portion (not shown) for fixing assembly 100 to the first bone portion. Fixation screw 50 can be a known bone screw or any other screw that can be used to secure a fixation device to bone. Although a fixation screw 50 is exemplified herein, the fixation screw 50 may include any suitable fasteners including shims, blades, nails, or the like.

Groove end 114 includes an upper portion 117 and a lower portion 118, defining a groove 120 therebetween and extending into first body portion 110, toward first screw end 112. Groove 120 is a space formed by a lower face 122 of upper portion 117 and an upper face 124 of lower portion 118. Lower face 122 has an arcuate face 126 that forms a concave arch, while upper face 124 has an arcuate face 128 that forms a convex arch, resulting in groove 120 having an arcuate shape.

Groove end 114 also includes a through-opening 130 extending through upper portion 117 and lower face 122 such that through-opening 130 is in communication with groove 120. Through-opening 130 can be threaded to threadingly engage securing member 170 to lower face 122. Alternatively, through-opening 130 can be unthreaded, as will be explained in further detail below.

Upper face 124 includes an opening 132 that extends from groove 120 away from groove 120. Opening 132 can be a through-opening that extends completely through lower portion 118. Alternatively, opening 132 can be a blind opening that does not extend completely through lower portion 118. If through-opening 130 is unthreaded, as alluded to immediately above, then opening 132 must be threaded to secure securing member 170 in openings 130, 132.

Second body portion 150 has a second fastener or screw end 152 and a tongue end 154, distal from second screw end 152. Second screw end 152 has a second fastener or screw hole 156 extending therethrough such that a fixation fastener or screw 52 can be inserted through second screw hole 156 and into a second bone portion (not shown) for fixing assembly 100 to the second bone portion. Like screw 50, fixation fastener or screw 52 can be a known bone screw, shim, blade, nail, or the like, or any other fastener normally used to secure a fixation device to bone.

The tongue end of second body portion 150 includes a tongue 158 extending outwardly from second body portion 150. As shown in FIG. 3, tongue 158 has an arcuate cross section such that tongue 158 is sized to fit into groove 120. In a first exemplary method to insert tongue 158 into groove 120, tongue 158 can be slid along a plane extending normal to the plane of the paper of FIG. 3. In an alternative exemplary method to insert tongue 158 into groove 120, tongue 158 is introduced to groove 120 at groove end 114 and inserted into groove 120 in a direction generally toward first screw end 112, curving tongue 158 through groove 120 as tongue 158 is advanced.

Referring to FIG. 4, tongue 158 has a tongue opening 168 aligned with through-opening 130 and second opening 132 such that through-opening 130 is in communication with second opening 132 through tongue opening 168. Tongue opening 168 is larger than through-opening 130. Tongue opening 168 can be circular or, alternatively, tongue opening 168 can be generally oval or oblong and extending axially along tongue 158.

Tongue 158 is slidingly inserted into groove 120 such that second body portion 150 is able to extend/contract and simultaneously pivot relative to first body portion 110. Lower face 122 and upper face 124 of groove 120 define a complimentary arcuate cross section for tongue 158 such that, when tongue 158 is inserted a first distance into groove 120, as shown in FIGS. 3 and 4, effectively contracting second body portion 150 a maximum distance into first body portion 110, tongue 158 pivots second body portion 150 such that second body portion 150 extends at a first angle relative to first body portion 110. As shown in FIG. 3, the angle δ is about 0-1 degrees. When tongue 158 is inserted a second distance into groove 120, as shown in FIGS. 5 and 6, effectively extending second body portion 150 away from first body portion 110, tongue 158 pivots second body portion 150 such that second body portion 150 extends at a second angle relative to first body portion 110, different from the first angle. As shown in FIG. 5, the angle β is about 3 degrees, although those skilled in the art will recognize that a maximum angle can be more than 3 degrees. Additionally, although not shown, second body portion 150 can be pivoted from first body portion 110 in a "negative" direction, meaning that second body portion 150 can be pivoted upwardly relative to first body portion 110. This extending/contracting and pivoting ability allows for insertion of assembly 100 in patients having slightly different anatomies, without having to bend or otherwise manipulate assembly 100.

Securing member 170 is threadingly connected to groove end 114 and extends through through-opening 130 for engagement with tongue 158 when tongue 158 is inserted between lower face 122 and upper face 124 of groove 120 to secure tongue 158 in groove 120 to secure tongue 158 between lower face 122 and upper face 124.

In an exemplary embodiment, securing member 170 is a fastener or screw that extends through through-opening 130 and tongue opening 168, and into second opening 132, with second opening 132 being threaded to threadingly engage with threads 172 on securing member 170. Securing member 170 includes a screw head 174 that is sized to mate with first opening 130, with first opening 130 being beveled to accept screw head 174 so that screw head 174 can be installed flush with the surface of first body portion 110. Screw threads 172 engage second opening 132 and pull upper face 124 toward tongue 158, while screw head 174 pulls lower face 122 toward tongue 158, sandwiching tongue 158 between lower face 122 and upper face 124 and using friction to retain second body portion 150 with respect to first body portion 110.

In an alternative exemplary embodiment, both first opening 130 and second opening 132 can be threaded so that securing member threadingly engages first opening 130 and second opening 132.

Figure 7:
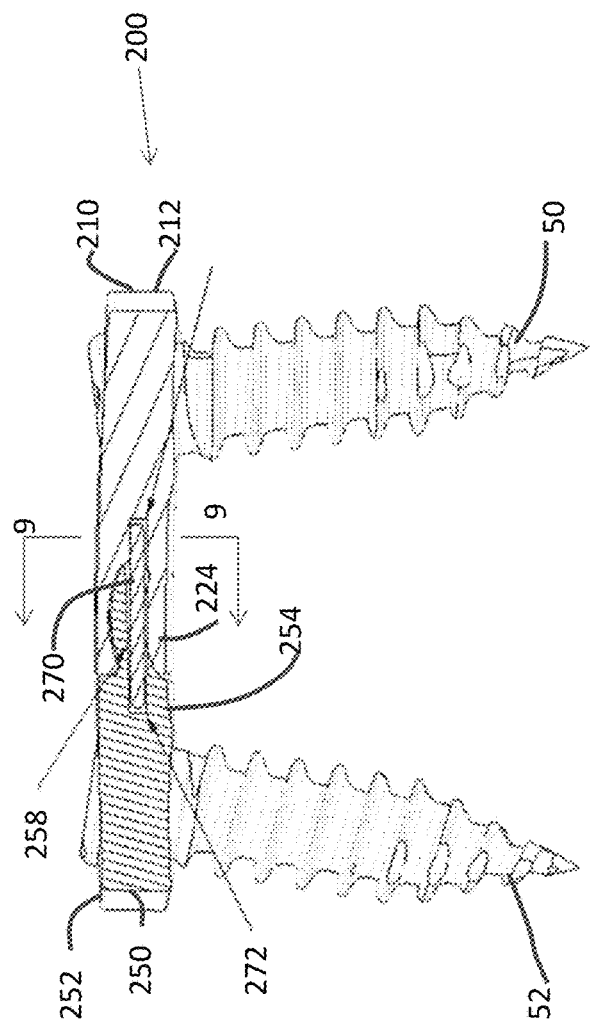
FIG. 7 is a sectional view of a hinge plate assembly according to a second exemplary embodiment.
Figure 8:
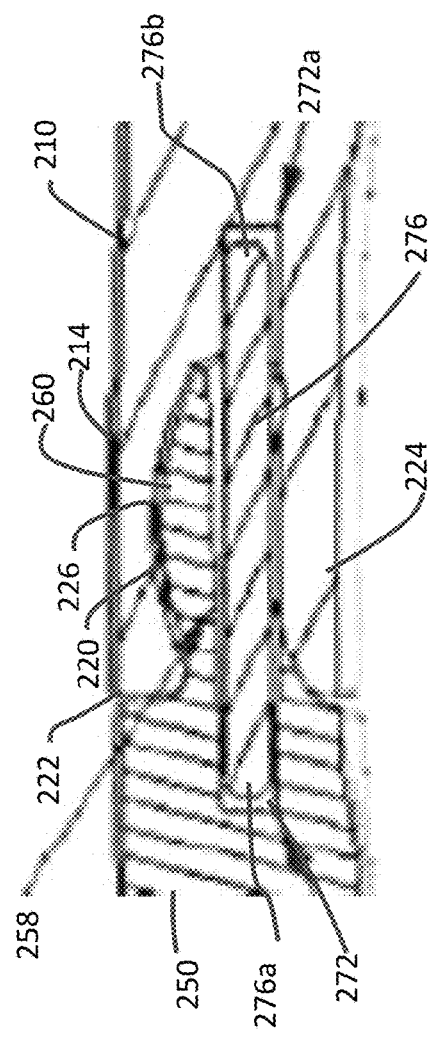
FIG. 8 is an enlarged view of a securing member used with the assembly shown in FIG. 7.
Figure 9:
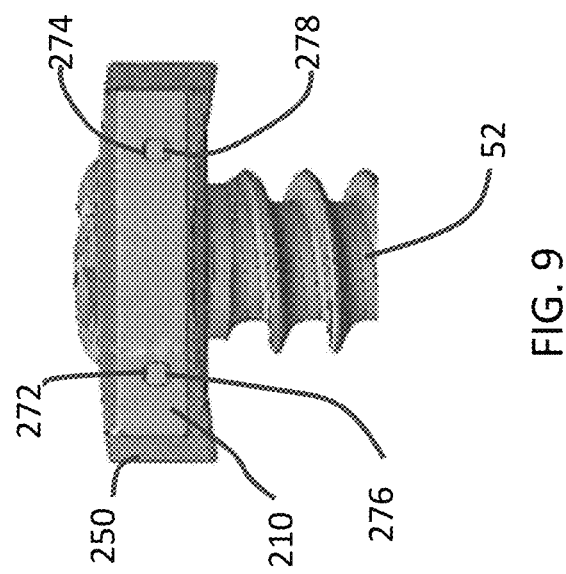
FIG. 9 is a sectional view of the hinge plate assembly of FIG. 7, taken along lines 9-9 of FIG. 7.

An alternative embodiment of a hinge plate assembly 200 ("assembly 200") is shown in FIGS. 7-9. Assembly 200 incorporates a first body 210 and a second body 250, similar to assembly 100 described above. First body 210 includes a first screw end 212 and a groove end 214, while second body portion 250 includes a second screw end 252 and a tongue end 254. Additionally, first body 210 includes a slot 220 for receiving a tongue 258. Slot 220 includes a top portion 222 and a bottom portion 224, with top portion 222 having a lower arcuate surface 226. Tongue 258 includes a convex arcuate surface 260 that mates with lower arcuate surface 226.

However, instead of securing member 170 being a screw, a securing mechanism includes a securing opening in the form of a first slot 272 and a second slot 274. Securing members 270 in the form of shims 276, 278 are inserted into a respective slot 272, 274 to secure first body portion 210 to second body portion 250. In an exemplary embodiment, shims 276, 278 are generally elongate cylindrical rods.

In an exemplary embodiment, shims 276, 278 are constructed from a memory material. Exemplary memory material can be selected from the group consisting of Nitinol and spring steel, although those skilled in the art will recognize that other memory materials can be used.

Shims 276, 278 can be elongate, straight rods at room temperature that flex to an arcuate shape after being inserted into a patient and warming to body temperature. The arcuate shape biases shims 276, 278 against tongue 258 to secure tongue 258 against groove 220 and restrict or prevent tongue 258 from moving relative to groove 220.

Second body portion 250 includes first slot 272 extending thereinto. First body portion 210 includes a first mating slot 272a that is axially aligned with first slot 272 so that a first end portion 276a of first shim 276 is inserted into first slot 272 and a second end portion 276b is inserted into first mating slot 272a. Similarly, first body portion 210 includes second slot 274 extending thereinto, while second body portion 250 includes a second mating slot (not shown) that is axially aligned with second slot 274 so that second shim 278 can be inserted into second slot 274 and the second mating slot. Shims 276, 278 are located directly below and in engagement with tongue 258 such that shims 276, 278 bias tongue 258 upwardly against lower arcuate surface 226 to retain first and second body portions 210, 250 together.

If it is desired to provide an angle between first body portion 210 and second body portion 250, second body portion 250 is expanded from first body portion 210 such that a portion of tongue 258 is pulled away from groove 220. Because of the mating nature of tongue 258 with lower arcuate surface 226, second body portion 250 pivots with respect to first body portion 210, generating the desired angle. Shims 276, 278 are flexible enough to allow such movement during insertion of assembly 200 into a patient and, as described above, when heated to body temperature, flex to bias tongue 258 upwardly against lower arcuate surface 226 to retain first and second body portions 210, 250 together.

The hinge plates 100, 200 may be moveable or adjustable before or after implantation, thereby allowing for better conformity with the anatomical structures which the hinge plate 100, 200 aligns with or contacts. The hinge plates 100, 200 may save time in not having to pre-bend plates to match patient anatomy, may minimize indecisions on how to pre-bend plates, and may minimize errors made while bending the plates. Additionally, the plates 100, 200 may provide a closer approximation to patient anatomy than traditional static plates.

It will be further understood that various changes in the details, materials, and arrangements of the parts which have been described and illustrated in order to explain the nature of this invention may be made by those skilled in the art without departing from the scope of the invention as expressed in the following claims.

What is claimed is:

1. A hinge plate assembly comprising:
   a first plate having:
   an upper surface, a lower surface adapted to be in contact with a bone;
   a first screw hole extending between the upper and lower surfaces;
   an arcuate groove extending into the first plate between the upper and lower surfaces; and
   a through-opening extending between the upper and lower surfaces and in communication with the groove;
   a second plate having a tongue extending outwardly therefrom and adapted to be inserted into the groove, a second screw hole extending through the second plate, the tongue having an arcuate shape complimentary to the groove, centers of the first and second screw holes defining a longitudinal axis; and a securing member extending through the through-opening for engagement with the tongue to secure the tongue in the groove;

wherein when the tongue is inserted a first distance into the groove, an upper surface of the second plate forms a first angle along the longitudinal axis in either downward or upward direction relative to the upper surface of the first plate, and when the tongue is inserted a second distance into the groove, the upper surface of the second plate forms a second angle along the longitudinal axis in either downward or upward direction relative to the upper surface of the first plate to allow the first and second plates to more closely conform to the bone surface contour.

2. The hinge plate assembly according to claim 1, wherein the tongue is slidably inserted into the groove.

3. The hinge plate assembly according to claim 1, wherein the second plate is extendable relative to the first plate.

4. The hinge plate assembly according to claim 3, wherein the second plate is pivotable relative to the first plate in a downward direction.

5. A hinge plate assembly comprising:

a first plate having an upper surface, a lower surface adapted to be in contact with a bone, a first screw hole, a first screw end and a groove end;

a second plate having a second screw hole, a second screw end and a tongue end, the tongue end being inserted into the groove end, centers of the first and second screw holes defining a longitudinal axis; and a securing member extending through the groove end and the tongue end, the securing member securing the tongue end in the groove end;

wherein when the tongue end is inserted a first distance into the groove end, an upper surface of the second plate forms a first angle along the longitudinal axis in either downward or upward direction relative to the upper surface of the first plate, and when the tongue is inserted a second distance into the groove, the upper surface of the second plate forms a second angle along the longitudinal axis in either downward or upward direction relative to the upper surface of the first plate to allow the first and second plates to more closely conform to the bone surface contour.

6. The hinge plate assembly according to claim 5, wherein the groove end comprises a threaded opening such that the securing member is threadingly connected to the groove end, and wherein the tongue end comprises an opening larger than the threaded opening.

7. The hinge plate assembly according to claim 5, wherein the tongue end comprises a tongue having an arcuate cross section.

8. The hinge plate assembly according to claim 7, wherein the groove end comprises a groove having a complimentary arcuate cross section.

9. The hinge plate assembly according to claim 7, wherein the groove end comprises an upper portion and a lower portion such that the tongue is inserted between the upper portion and the lower portion and wherein the securing member is adapted to secure the tongue between the upper portion and the lower portion.

* * * * *